United States Patent [19]
Okubo

[11] Patent Number: 5,641,230
[45] Date of Patent: Jun. 24, 1997

[54] METHOD OF DETERMINING CLOUD POINTS AND CLOUD POINT METER

[75] Inventor: Shuichi Okubo, Tokyo, Japan

[73] Assignee: Japan Energy Corporation, Tokyo, Japan

[21] Appl. No.: 351,456

[22] PCT Filed: Mar. 24, 1994

[86] PCT No.: PCT/JP94/00471

§ 371 Date: Dec. 13, 1994

§ 102(e) Date: Dec. 13, 1994

[87] PCT Pub. No.: WO94/24544

PCT Pub. Date: Oct. 27, 1994

[30] Foreign Application Priority Data

Apr. 15, 1993 [JP] Japan ................ 5-111170
Nov. 16, 1993 [JP] Japan ................ 5-308546

[51] Int. Cl.$^6$ ................................ G01N 25/12
[52] U.S. Cl. ................ 374/20; 374/19; 356/339
[58] Field of Search ................ 374/17, 18, 19, 374/20; 356/339

[56] References Cited

U.S. PATENT DOCUMENTS

| | | | |
|---|---|---|---|
| 3,077,764 | 2/1963 | Kapff | 374/19 |
| 3,527,082 | 9/1970 | Pruvot et al. | 374/17 |
| 3,807,865 | 4/1974 | Gordon et al. | 374/17 |
| 4,045,971 | 9/1977 | Brenner, Jr. | 374/20 |
| 4,083,224 | 4/1978 | Gayst | 374/19 |
| 4,804,274 | 2/1989 | Green | 374/17 |
| 5,007,733 | 4/1991 | Laurent et al. | 356/338 |
| 5,022,045 | 6/1991 | Elliott | 374/20 |
| 5,088,833 | 2/1992 | Tsang et al. | 374/20 |

FOREIGN PATENT DOCUMENTS

| | | | |
|---|---|---|---|
| 2366557 | 4/1978 | France | 356/339 |
| 40-24319 | 10/1965 | Japan . | |
| 0007550 | 1/1983 | Japan | 374/17 |
| 61-17941 | 1/1986 | Japan . | |
| 63-132139 | 6/1988 | Japan . | |
| 1-170838 | 7/1989 | Japan . | |
| 2-114151 | 4/1990 | Japan . | |
| 0168138 | 6/1990 | Japan | 356/339 |
| 1684632 | 10/1991 | U.S.S.R. | 356/339 |

OTHER PUBLICATIONS

Abstract of GB 1,438,754, complete specification published on 9 Jun. 1976.
Hach CR "Surface Scatter" Turbidimeter, Model 1032, Hach Chemical Company, Ames, Iowa (Nov. 1964).

*Primary Examiner*—Diego F. F. Gutierrez
*Attorney, Agent, or Firm*—Panitch Schwarze Jacobs & Nadel, P.C.

[57] ABSTRACT

A method of determining cloud points is provided which comprises: bringing a sample into contact with a high precision cloud point meter which includes a waveguide sensor of a total-reflection type connected to both incidence and emergence optical fibers and a cooling/heating means located in contact with the total-reflection type sensor to cool/heat it within a desired temperature range; cooling/heating the sample; and then determining the sample temperature at which total-reflection of light has taken place as the cloud point of the sample. The sensor includes a waveguide of a structure which consists of an incidence channel and an emergence channel formed on a substrate and which intersect along a detection surface with which a liquid whose cloud point is to be determined comes in contact. An incidence optical fiber is connected to the entrance of the incidence channel to introduce of light into the channel, and an emergence optical fiber is connected to the exit of the emergence channel to receive total reflected light from the channel. Alternatively, a waveguide is formed which comprises an incidence region and an emergence region both of which are adjacent to the detection surface, and an incidence channel intersecting the incidence region and a plurality of emergence channels intersecting the emergence region. The cooling/heating means is preferably a Peltier element mounted on a heat sink.

6 Claims, 5 Drawing Sheets

METHOD OF DETERMINING CLOUD POINTS AND CLOUD POINT METER

TECHNICAL FIELD

This invention relates to a method of determining cloud points and a cloud point meter useful for the method. More particularly, this invention relates to a method of determining cloud points and a cloud point meter which use a total-reflection type wave-guide sensor connected to optical fibers to determine clouding, a phenomenon caused by the deposition or separation of solid matter, water removal, or other change in state or condition, of liquid products of chemical industry, especially petroleum products such as gas oil in the petroleum industry.

BACKGROUND ART

Gas oil, a product from the petroleum refining process, contains paraffins. Since paraffins are solid at about room temperature, an increase in the paraffin content will reduce the fluidity of the gas oil at low temperatures as in winter. When a sample of petroleum product, such as gas oil or lubricating oil, is gradually cooled in a prescribed way, its paraffin content deposits or separates increasingly until the walls of the container holding the sample begins to appear cloudy. This point is known as a cloud point. The same phenomena occur with plasticizers and surfactants. Cloud point determination is important for the specifications of petroleum products in winter. There are many other cases in which the deposition of solids upon cooling of petroleum products must be determined.

Japanese Industrial Standards K-2269 prescribes testing procedures for the cloud point of petroleum products as well as the fluid point of crude oil and petroleum products. The cloud point testing procedure is briefly defined: "Place a test tube holding 45 ml of a sample into an outer tube in a cooling bath and cool it in a prescribed manner. Take out the test tube each time the sample temperature has dropped by 1° C. The temperature at which a cloudy appearance has just been seen in the bottom of the sample shall be deemed a cloud point." Remarks say: "The use of an automatic cloud point tester instead is permissible provided it is confirmed beforehand in conformity with JIS Z-8402 that there is no significant difference between the result thereby attained and the result obtained by the testing procedure defined above." As the testing equipment are furnished: a test tube in the center of which a test thermometer is held vertically with a cork stopper in place, outer tubes each fitted with a bottom disk of cork or felt and adapted to house the test tube therein, and cooling baths each equipped with a thermometer for cooling solution. The test tube is able to be placed into and taken out of an outer tube through an annular gasket kept in close contact with the outer wall of the test tube. The annular gasket tightly fitted around the test tube is loosely in contact with the outer tube to support the test tube vertically therein. The testing procedure is specified to comprise:

(1) keeping a sample at a temperature higher than a predicted cloud point by at least 14° C.;

(2) pouring the sample into the test tube up to the height of a marked line (at the middle);

(3) hermetically sealing the test tube with the cork stopper fitted with a thermometer, in such manner that the thermometer is held upright in the center, with its tip in contact with the bottom of the tube;

(4) placing the test tube together with the annular gasket into the outer tube fitted with a bottom disk;

(5) placing the outer tube, together with the test tube housed therein, into a first cooling bath and supporting the outer tube lest it float 25 mm or more from the surface of the cooling solution;

(6) after the sample temperature has reached the vicinity of the predicted cloud point, taking out the test tube upon each drop by ° C., rapidly and without causing any sample vibration, inspecting the sample for any cloudy appearance seen in the bottom, and then placing the test tube back into the outer tube; and (7) repeating these steps and recording the reading of the thermometer at the moment when visible clouding or haze appears for the first time in the bottom of the sample. (In case when clouding is not observed with a sample that has been cooled down to 10° C., the test tube shall be transferred to an outer tube in a second cooling bath at a lower temperature. If clouding is still not observed at a sample temperature of −7° C., the test tube shall be transferred to an outer tube in a third cooling bath at a much lower temperature.)

Thus the procedure requires bothersome handling; repeatedly placing the test tube into the outer tube taking it out carefully by hand.

The United States too has similar provisions.

The automatic cloud point tester used there, for petroleum products, is such that a container holding about 50 cc of a sample is placed in a cooling tank, cooled at a cooling rate of 2° C./min, and deposition of paraffins is detected by a light absorption or diffusion method.

That automatic cloud point testing method faithfully follows the principle of cloud point determination. Actually, the sampling container has too large a capacity to ensure at all times the uniformity of temperature of the substance being tested. The measurement time is prolonged because the cooling from room temperature down to −20° C. takes much time. Moreover, the sample must be introduced each time into a large container, and this sampling is a troublesome work requiring both time and labor. The detection by the light absorption or diffusion method that depends on a certain amount of deposit for judgment lacks accuracy. Each run for cloud point determination takes a period of about 60 minutes.

The object of the this invention is to develop a novel technique for accurately determining the cloud points of petroleum products in a simpler and quicker way than heretofore.

DISCLOSURE OF INVENTION

We perceived the fact that, in the case of gas oil, for example, there is a difference in refractive index between gas oil and paraffins. We then conceived of exploiting the refractive index difference in the determination of cloud points in terms of changes in light refraction and total reflection conditions. Intensive research was made on this basis to develop a small-size cloud point meter. The research has led to the conclusion that a combination of a waveguide sensor of a total reflection type connected to optical fibers and a cooling/heating means is the most suitable for the purpose. Trial manufacture proved that a meter of the above combination performed satisfactorily. Thus, the present invention provides a method of determining cloud points characterized by the steps of: bringing a sample into contact with a high precision cloud point meter which includes a waveguide sensor of a total-reflection type connected to both incidence and emergence optical fibers and a cooling/heating means located in contact with the total-reflection type sensor to cool/heat it within a desired temperature range cooling/heating the sample; and then determining the sample temperature at which total reflection of light has taken place as the cloud point of the sample.

As a cloud point meter useful for carrying the above method into practice, the invention provides (A) a cloud point meter characterized by: a waveguide sensor of a total-reflection type including a waveguide of a structure which consists of an incidence channel and an emergence channel formed on a substrate and which intersect along a detection surface with which a liquid whose cloud point is to be determined comes in contact, an incidence optical fiber connected to the entrance of the incidence channel to introduce light into the channel, and an emergence optical fiber connected to the exit of the emergence channel to receive total reflected light from the channel; and a cooling/ heating means located in contact with the total-reflection type waveguide sensor to cool/heat the latter within a desired temperature range.

The above cloud point meter has but one emergent channel intersecting the incident channel along the detection surface. This structure sometimes allows the rays ordinarily not conforming to the conditions for total reflection to intrude into the emergent channel, thereby reducing the accuracy of measurement. As an improvement over this, it has just been found that only the light of preset angles of emergence can be detected by forming on a substrate a waveguide of a structure which consists of incidence and emergence regions formed adjacent to a detection surface with which a liquid whose cloud point is to be determined comes in contact, an incidence channel which intersects the incidence region, and a plurality of emergence channels which intersect the emergence region, and then connecting a plurality of emergence optical fibers to the respective exits of the emergence channels. On the basis of this discovery, the present invention also provides a cloud point meter characterized by: a waveguide sensor of a total-reflection type which comprises a substrate, an incidence region and an emergence region both of which are formed adjacent to a detection surface with which a liquid whose cloud point is to be determined comes in contact, a waveguide layer formed on the substrate to provide a waveguide of a structure which consists of an incidence channel intersecting the incidence region and a plurality of emergence channels intersecting the emergence region, an incidence optical fiber connected to the entrance of the incidence channel to introduce light into the channel, and a plurality of emergence optical fibers connected to the respective exits of the emergence channels to receive total reflected lights from the channels; and a cooling/heating means located in contact with the total-reflection type waveguide sensor to cool/heat the latter within a desired temperature range. The cooling/ heating means is a Peltier element mounted on a heat sink, a heat exchanger which uses a circulating coolant, or a cryostat.

BEST MODE FOR CARRYING OUT THE INVENTION

As is generally known, light incident from a medium 1 of a given refractive index ($n_1$) on a secondary medium 2 of a different refractive index ($n_2$) along the boundary surface refract in accordance with what is known as Snell's law, but the light incident at a larger angle than the critical angle $\theta_c$ defined as $\sin \theta_c = n_2/n_1$ is totally reflected. In the case of a petroleum product, e.g., gas oil, its refractive index at 20° C. is 1.469, and the refractive indices of paraffins range from 1.412 to 1.460 ($C_{10}$=1.412, and $C_{20}$= 1.455). The temperature at which the deposition or separation of solid matter can be detected by the following settings. The angle of incidence of light into an incidence region of an incidence channel of a waveguide connected to an optical fiber, the emitrance angle range of an emitrance region leading to a plurality of emitrance channels, and the refractive index of the waveguide are all set to detect, e.g., only a given preset angle of emitrance at which the deposition of paraffins takes place. Also to be set is a necessary temperature control range, e.g., from 30° C. to −15° C., inclusive of the temperature at which the deposition or separation of the solid matter is caused by cooling means. The incident light from the incidence optical fiber refracts through the detection surface into the test liquid material before the latter reaches the cloud point. When the cloud point has been reached and the deposition of solid matter has occurred, the total reflection condition of the detection surface changes and the output of the emergence optical fiber changes too. The temperature at this point is read out from a temperature-measuring device attached to the junction between a Peltier element as cooling/heating means and the substrate of a sensor. The combination of the waveguide structure used and a small localized cooling/ heating means like a Peltier element reduces the heat capacity of the instrument. The use of a substrate with good heat transfer enhances measurement controllability as well as temperature controllability. The possibility of malfunctioning can be lessened by providing an emergence region larger than the incidence region, a plurality of emergence channels connected to the emergence region, and optical fibers connected to the respective regions.

Figure 1:
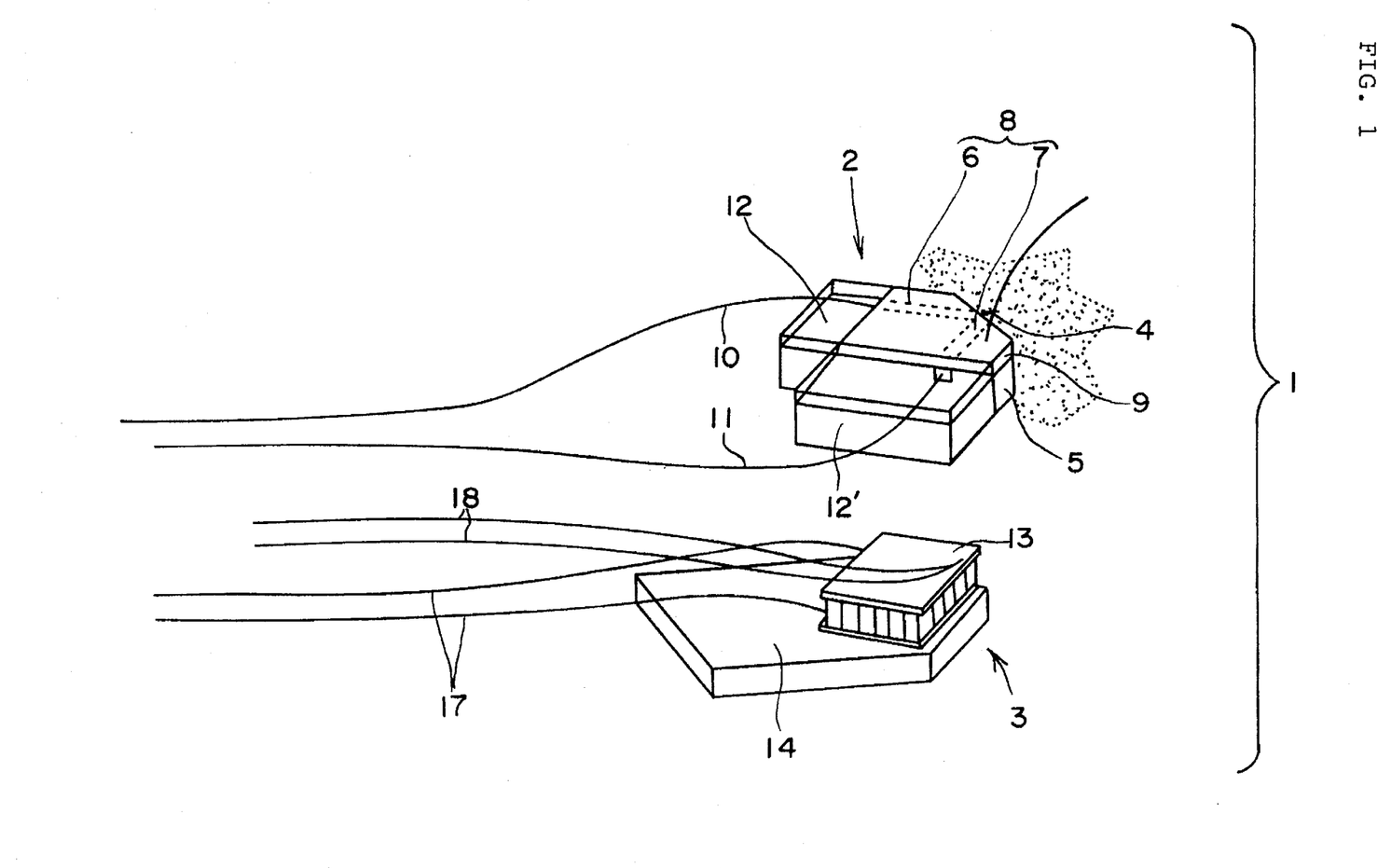
FIG. 1 is a disassembled perspective view of a first embodiment of the cloud point meter of this invention.

FIG. 1 is a disassembled perspective view of a first embodiment of the cloud point meter of this invention. The cloud point meter 1 is made up of a waveguide sensor 2 of a total-reflection type and a cooling/heating means 3 located in contact with the total-reflection type sensor (although shown separately by way of illustration). The total-reflection type waveguide sensor 2 has a detection surface (liquid-contacting surface) 4 for contact with the gas oil or other petroleum or chemical product M whose cloud point is to be determined.

The total-reflection type waveguide sensor 2 comprises a substrate 5 and a waveguide layer 9 provided thereon and which is formed with a waveguide 8 consisting of an incidence channel 6 and an emergence channel 7 which intersect along the detection surface 4. The sensor is fitted with an incidence optical fiber 10 connected to the entrance of the incidence channel to introduce incident rays into the channel and also with an emergence optical fiber 11 connected to the exit of the emergence channel to receive the total-reflection light from that channel. The incidence optical fiber 10 and the emergence optical fiber 11 are connected, respectively, to the incidence channel 6 and the emergence channel 7 in the waveguide layer 9 via junction bases 12, 12'. The incidence optical fiber 10 is connected at the other end to a light source, e.g., an He-Ne laser. The emergence optical fiber 11 is connected at the other end to a suitable optical detector means.

The waveguide 8 is made by forming thin films corresponding to the core and cladding of an optical fiber, in succession, over a substrate, so as to guide the light waves. It may take any of well-known configurations such as (a) ridge, (b) buried or embedded, and (c) loaded type. For the fabrication of the waveguide, any of the techniques relying upon epitaxial growth, molecular or particle deposition such as CVD or PVD, or ion doping may be used. For the purposes of this invention doping $SiO_2$ films with $GeO_2$ is practical. The incidence channel 6 and the emergence channel 7 are formed at proper angles of intersection to meet along the detection surface 4 so that the lights traveling the incidence channel can refract and perform total internal reflection depending on the state of the material with which the light comes in contact at the detection surface 4.

The junction bases of the optical fibers can be formed by inserting the optical fibers through grooves provided on a Si substrate and securing the fibers in place with an adhesive such as an epoxy resin.

The cooling/heating means 3 functions to cool/heat a sample at all times, within predetermined temperature ranges at which the total reflection sensor is enabled to detect a change of state or condition such as the deposition of solid matter. The cooling/heating means 3 is preferably built up of what is known as a Peltier element, or a semiconductor of Group V–VI compounds, e.g., $Bi_2Te_3$, $Sb_2Te_3$, $Bi_2Se_3$, and their solid solutions, jointed to impurity-doped p-type and n-type semiconductors, and cooling and heat-dissipating regions attached to the top and bottom of the unit. Such cooling/heating means are commercially available under the trade names of "Cooling unit" or "Thermomodule." In the accompanying drawings a Peltier element 13 is shown mounted on a heat sink 14 of copper. Power cables 17 are connected to the unit for the supply of a current to the semiconductors. Such a cooling/heating means is ideal for the purposes of this invention in that it permits local cooling without any moving part but with a very small and simple construction. For example, a unit in which Peltier elements are built up in two steps in cascade fashion can perform the temperature control in the range from 30° C. down to −15° C. that is specified to be essential under this invention. The cooling/heating means is located with its top in contact with the total-reflection type sensor and its bottom on the heat sink of copper plate or the like. It may be replaced by or used in combination with some other means designed to cool/heat the whole total-reflection type sensor, such as a heat exchanger using a circulating cooling medium or a cryostat that exploits adiabatic expansion upon release of a compressed gas. A thermocouple 18 is attached to the junction between the Peltier element 13 and the sensor substrate 5.

Figure 2A:
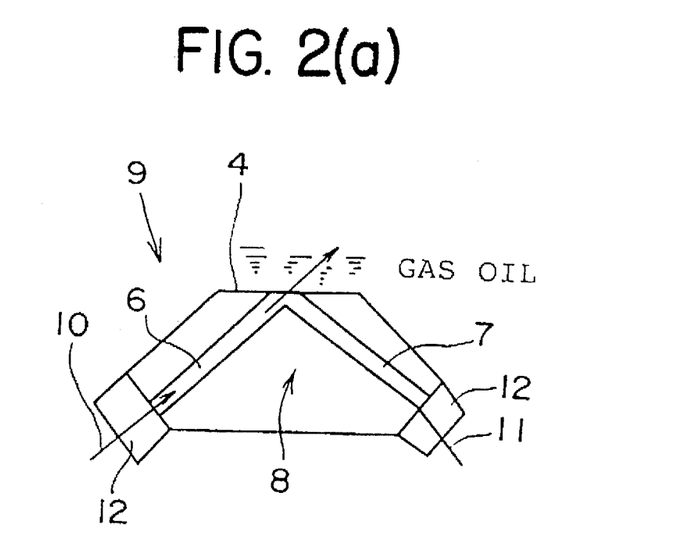
FIGS. 2(a) and 2(b) illustrate the first embodiment applying the principle of the present invention to a petroleum product, FIG. 2(a) showing the petroleum product not reaching its cloud point yet and the incident light being refracted into the product and FIG. 2(b) showing paraffins deposited or separated onto the detection surface, with consequent total reflection of the incident light through the emergence channel into the emergence optical fiber.
Figure 2B:
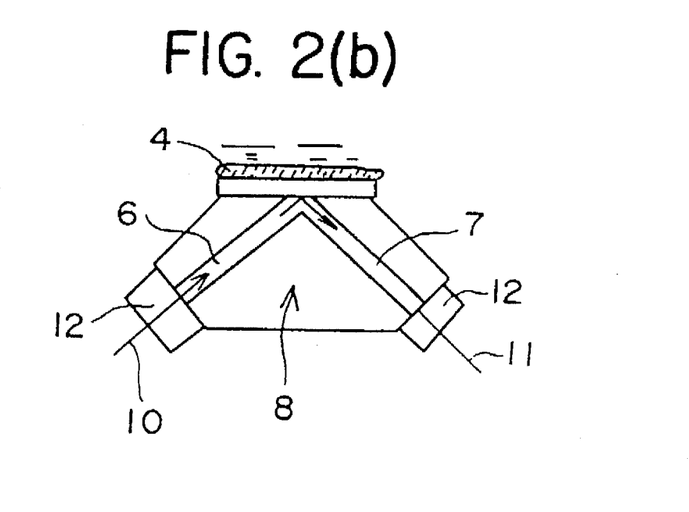

FIGS. 2(a) and 2(b) illustrate the principle of the present invention as applied to a petroleum product. FIG. 2(a) shows the petroleum product not reaching its cloud point yet and the incident light refracted into the product. FIG. 2(b) shows paraffins deposited or separated onto the detection surface, with consequent total reflection of the incident light through the emergence channel into the emergence optical fiber. In the case of gas oil, its refractive index at 20° C. is 1.469 and the index of paraffins ranges from 1.412 to 1.460 ($C_{10}$=1.412, $C_{20}$=1.455). On-off control of the refraction and total reflection or other operations becomes possible when, for example, the angle of incidence into the waveguide is set to 81° and the angle of reflection too to 81° (the refractive index of the waveguide=1.458, the refractive index that produces total reflection=1.440). The same applies to other petroleum products, such as gasoline and lubricating oil, and many other chemical products. In those cases again the incidence and reflection angles and the refractive index of the waveguide are set so that total reflection can result from a change in the refraction index with the deposition or separation of the paraffin or other solids content from the test material.

In this way a cloud point meter is obtained which indicates by a binary (on-off) system the point of time at which the deposition or separation of solid matter has just taken place. If the cloud point meter is kept in contact with a petroleum or other chemical product and the temperature control is rapidly carried out, it will be possible continually to detect the cloud point at individual temperature cycles. Thus a small-size quick response cloud point meter is obtained. Compared with the conventional method that takes about 60 minutes for a measurement, the sensor according to this invention needs a strikingly shortened period of only about 60 seconds for the detection of the cloud point, rendering it possible to achieve extremely efficient measurement.

The cloud point meter thus far described has but one emergent channel intersecting the incident channel along the detection surface. This structure sometimes allows the lights ordinarily not conforming to the conditions for total reflection to intrude into the emergent channel, thereby reducing the accuracy of measurement.

Figure 3:
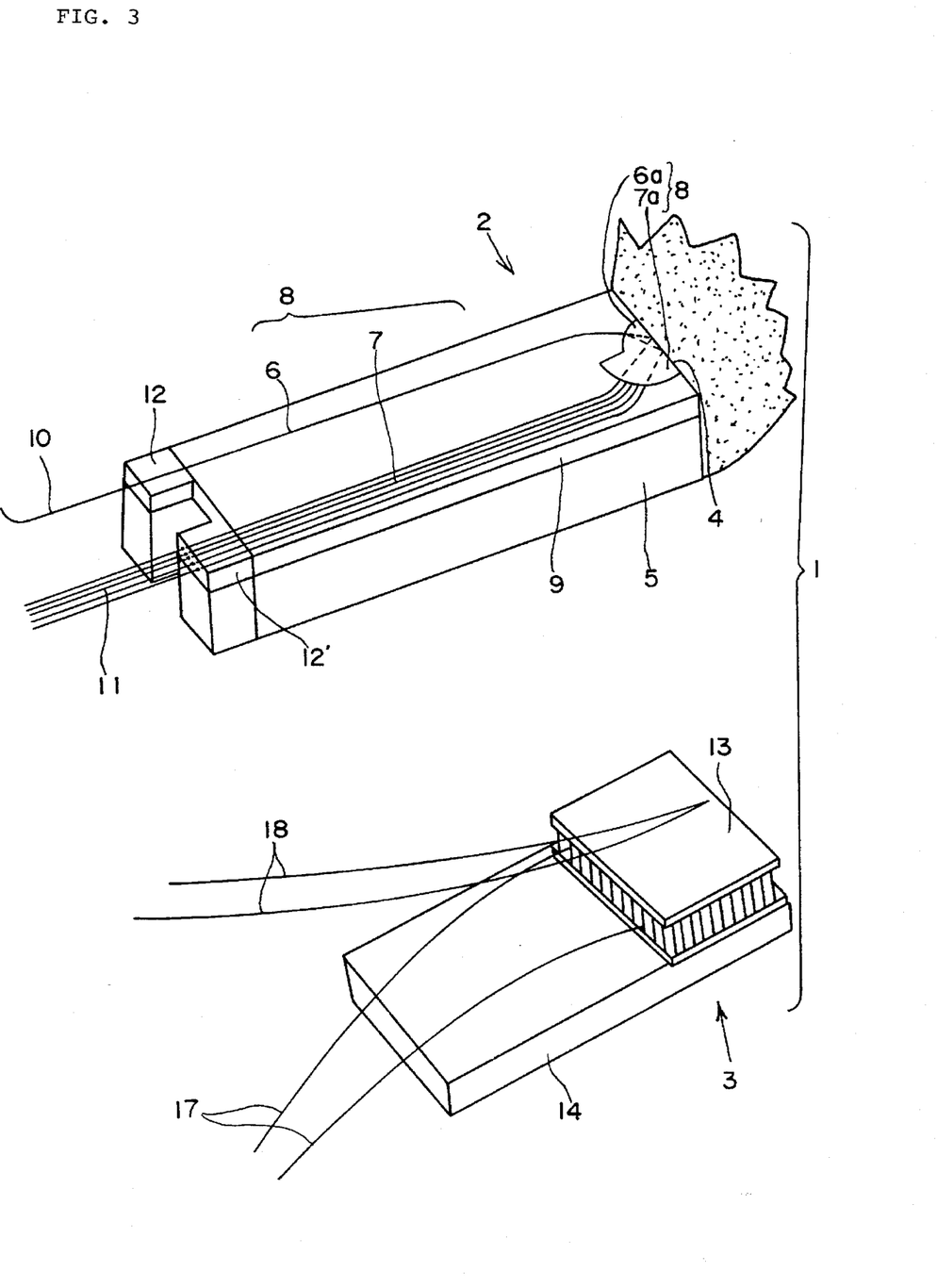
FIG. 3 is a disassembled perspective view of a second embodiment of the cloud point meter of this invention.

FIG. 3 is a disassembled perspective view of a second embodiment of the cloud point meter of this invention. Parts like those in FIG. 1 are like numbered. The cloud point meter 1 consists of a waveguide sensor 2 of a total-reflection type and a cooling/heating means 3 located in contact with the total-reflection type sensor (shown as separated by way of illustration). The total-reflection type waveguide sensor 2 has a detection surface (liquid-contacting surface) 4 that comes in contact with the gas oil or other petroleum or chemical product M whose cloud point is to be determined. The total-reflection type waveguide sensor 2 comprises a substrate 5 and a waveguide layer 9 provided thereon and which is formed with an incidence channel 6, emergence channels 7, an incidence region 6a, and an emergence region 7a, both of the regions being formed adjacent to the detection surface 4. The incidence channel 6 intersects the incidence region 6a and the plurality of (five, in this case) emergence channels intersect the emergence region 7a. The sensor is fitted with an incidence optical fiber 10 connected to the entrance of the incidence channel 6 to introduce incident rays into the channel and also with emergence optical fibers 11 connected to the respective exits of the emergence channels 7 to receive the total-reflection rays of light from those channels. The incidence optical fiber 10 and the emergence optical fibers 11 are connected, respectively, to the incidence channel 6 and the emergence channels 7 of the waveguide layer 9 via an optical fiber junction base 12 and an optical fiber array junction base 12'. The incidence optical fiber is connected at the other end to a laser light source, e.g., a semiconductor laser or He-Ne laser source. The array of emergence optical fibers is connected at the other end to a suitable optical detector means.

The waveguide 8, like the counterpart of the above-described embodiment, is made by forming thin films corresponding to the core and cladding of an optical fiber, in succession, over a base, so as to guide the light waves. It may be formed to any of well-known configurations such as (a) ridge, (b) buried or embedded, and (c) loaded type. For the fabrication of the waveguide, any of the techniques relying upon epitaxial growth, molecular or particle deposition such as CVD or PVD, or ion doping may be used. For the purposes of this invention doping $SiO_2$ films with $GeO_2$ is practical. The incidence channel 6 and the emergence channels 7 are designed to intersect the incidence region 6a and the emergence region 7a adjacent to the detection surface 4, so that the light from the incidence channel pass through the incidence region where they are diffused to some extent before reaching the detection surface, and they are refracted or totally reflected depending on the state or condition of the material with which the light comes in contact along the detection surface. Where total reflection takes place, the whole reflected light travels through the emergence region into the plurality of emergence channels 7 at preset angles.

The junction bases 12, 12' of the optical fiber and fiber array can be formed by inserting the optical fibers through grooves provided on a Si substrate and securing the fibers in place with an adhesive such as an epoxy resin.

The cooling/heating means 3 is the same as that already described in connection with the first embodiment.

Figure 4A:
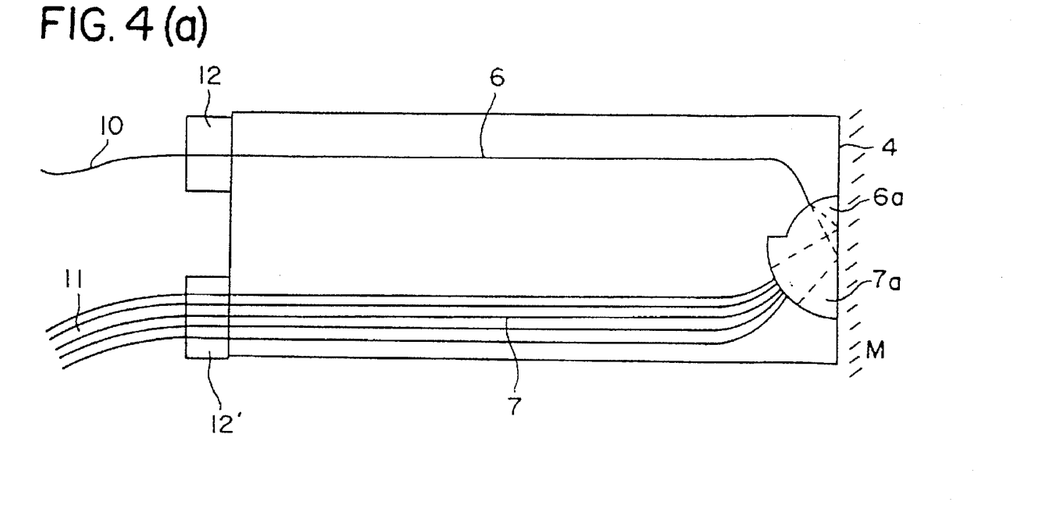
FIGS. 4(a), 4(b) and 4(c) show the waveguide of the second embodiment in detail, FIG. 4(a) being a top view of a waveguide sensor of a total-reflection type, FIG. 4(b) an enlarged view of an incidence region and an emergence region along a detection surface, and FIG. 4(c) an explanatory view of the incidence region.
Figure 4B:
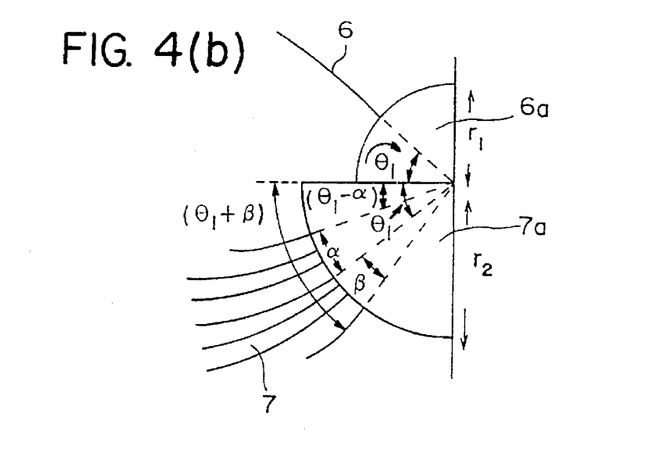
Figure 4C:
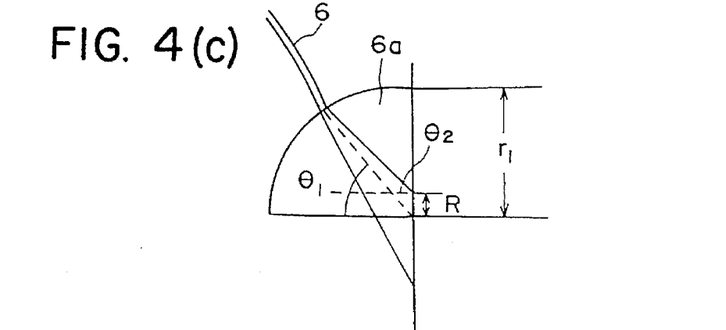

FIGS. 4(a), 4(b) amd 4(c) show the waveguide of the second embodiment in detail. FIG. 4(a) is a top view of the waveguide sensor 2 of the total-reflection type; FIG. 4(b) is an enlarged view of the incidence region 6a and the emergence region 7a along the detection surface 4; and FIG. 4(c) is an explanatory view of the incidence region 6a. The incidence region 6a preferably has the shape of a quadrant with a radius $r_1$, into which the incidence channel 6 extends with an incidence angle $\theta_1$. The angle $\theta_1$ is determined by the boundary value $\sin \theta_1 = n_2/n_1$ that Snell's law leads to as the condition for total reflection, where $n_1$ is the refractive index of the waveguide and $n_2$ is the refractive index of the deposit that is formed below the cloud point.

The emergence region 7a too is preferably formed as a quadrant with a radius $r_2$. The emergence region 7 is designed to have an array of n emergence channels formed within an angular range from $(\theta_1-\alpha)$ to $(\theta_1+\beta)$. (Here $r_x$ is to be given in μm, and $\theta_1$, $\alpha$, and $\beta$ in radians.) A combination of the regions where $r_2$ is greater than $r_1$ is easier to design. Incident rays of light travel somewhat fanwise to reach the detection surface as indicated at (c). Where total reflection takes place, all the reflected rays of light are so reflected within the range from $(\theta_1-\alpha)$ to $(\theta_1+\beta)$ to pass through certain of the plurality of emergence channels.

In designing the waveguide, it is recommended to take into account or actually take up the following conditions ($r_x$ in μm, and $\theta_1$, $\alpha$, and $\beta$ in radians):

(1) For the prevention of intermode connection of the adjacent emergence channels on the emergence side, the condition to be adopted desirably is:

$r_2 (\alpha+\beta)/(n-1) \geq 18$ (2) The refractive index to be detected at an angle $(\theta_1+x)$ is to conform to Snell's law as follows:

$\sin \theta_1 / \sin (\theta_1+x) = n_2/n_1$ (3) The range of $r_1$, over the distance R from the center of spread of the incident light mode at the detection surface to the farthest end point, is restricted to:

$r_1 \cos \theta_1 (\tan \theta_1 - \tan \theta_2) = R$ (where the range of R is $10 \geq R \geq 200$, e.g., $\theta_1=69°$ and $\theta_2=69°-4°=65°$).

The waveguide must be curved in part, but it is desirable that each bend be within an angle of 2° and each pass have a length of at least 100 μm.

The incidence channel too may be increased in number to a plurality under the condition (1).

When machining the incidence and emergence regions of the sensor, the incidence angle/emergence angle can be altered by changing the cutting angles with respect to the centers of $r_1$ and $r_2$. Consequently, a single mask pattern is applicable to a broad range of refractive indices.

Similarly, cloud point determination can be accomplished with gasoline, lubricating oil, and other petroleum products and also with many other chemical products as well. The angles of incidence and reflection and also the refractive index of the waveguide are set so that when the deposition or separation of paraffins and other solids takes place, a corresponding change in the refractive index causes total reflection.

Figure 5:
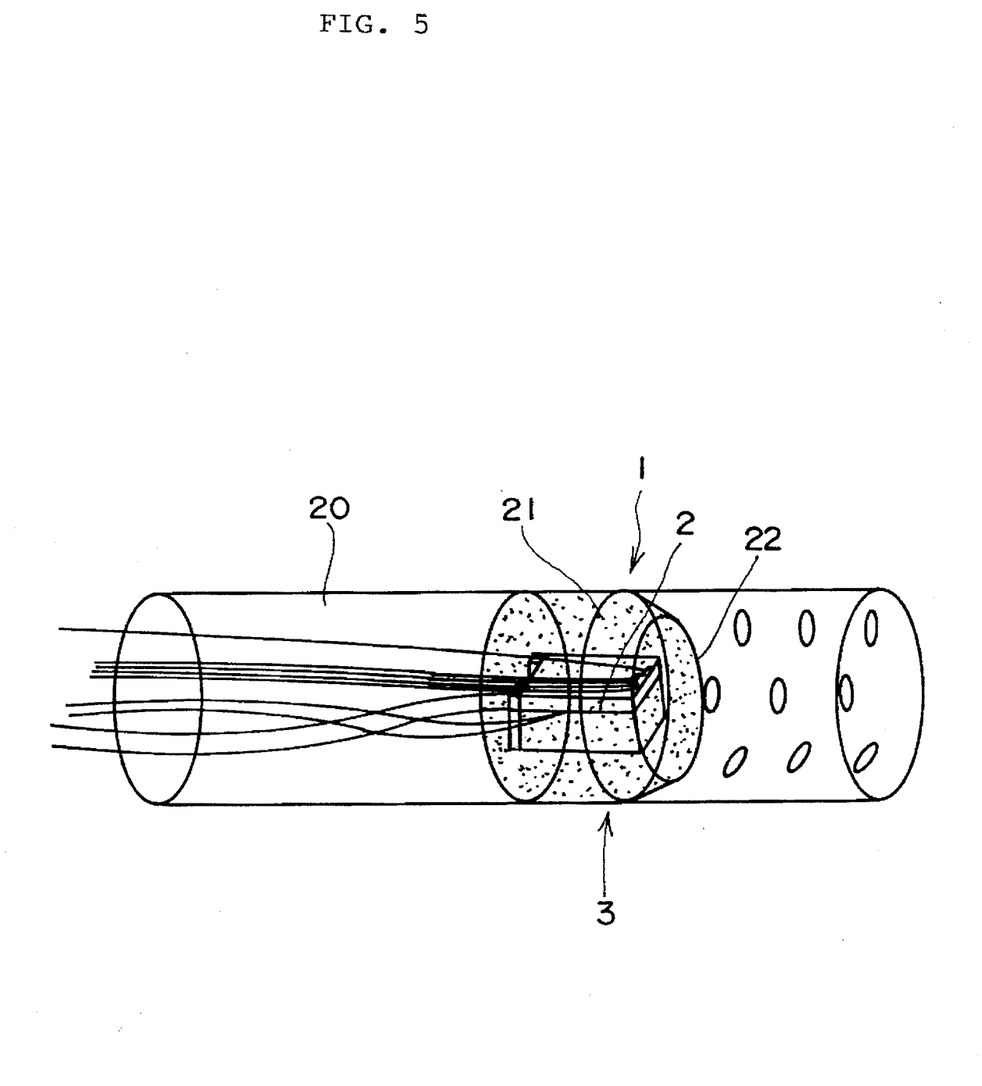
FIG. 5 illustrates a cloud point meter probe comprising a measuring cylinder and a cloud point meter of this invention buried with its detection surface held at the front end in a mass of glass within the cylinder.

FIG. 5 illustrates a cloud point meter probe comprising a measuring cylinder 20 and a cloud point meter consisting of a total-reflection type waveguide sensor 2 and a cooling/heating means 3 disposed under the sensor, the cloud point meter being buried with its detection surface held at the front end in a mass of glass 21 within the cylinder. A detection region 22 is located inside the front end portion of the measuring cylinder which is perforated.

Thus, according to this invention, a cloud point meter is obtained which indicates, by a binary (on-off) method, the point of time at which the deposition or separation of solid matter has just occurred. The detection of the cloud point is easy and reliable because the meter has only to detect the rays of light of preset angles of emergence in the plurality of emergence optical fibers. The construction in which the waveguide channels of the waveguide layer are formed on a substrate permits incident light to reach the detection end efficiently; it thus enables inexpensive light-emitting-receiving elements to constitute a sensor. The quantity of sample required for the cloud point determination can be smaller than that needed by the cloud point meter specified in JIS. One milliliter of sample is enough for determination under this invention, whereas 50 ml is required for the JIS procedure. The thermal uniformity of the sample is naturally improved. Good heat response and hence high-speed determination are made possible by the use of a sensor with a small heat capacity, especially by the use of an Si substrate (0.6 cm³ in size) with desirable heat transfer characteristics. The determination is sped up from the rate of 2° C./min according to the JIS method to 30° C./min under this invention. Continual cloud point determination for individual temperature cycles can be realized by keeping the cloud point meter in contact with petroleum or other chemical product whose cloud point is to be determined and by performing temperature control rapidly. A cloud point meter small in size and capable of high-speed response is thus obtained. Compared with the conventional method of cloud point determination that takes about 60 minutes per measurement, the sensor of this invention shortens the period to but about 60 seconds, achieving very efficient measurement.

EXAMPLES

A waveguide was formed by depositing $SiO_2$ as a cladding and $SiO_2$ and $GeO_2$ together as a core, both by CVD, on a Si substrate. The cladding had a 20 μm thickness and the core was 6 μm thick and 6 μm wide. The design conditions for the incidence and emergence regions were: $n_0=1.458$; $n_1=1.510$; $\theta_1=69°$; $\alpha=\beta=2°$; $r_1=1.0$ mm; $r_2=1.6$ mm; and n=5. Quartz SM fibers (core dia. 6 μm) for 0.85 μm wavelength were used as incidence/emergence optical fibers. The critical refractive indices at the emergence ends 1 to 5 were as listed in Table 1.

TABLE 1

| Emergence end No. | Angle of emergence | Refractive index |
|---|---|---|
| 1 | 73° | 1.445 |
| 2 | 71° | 1.428 |
| 3 | 69° | 1.410 |
| 4 | 67° | 1.390 |
| 5 | 65° | 1.368 |

A Peltier element was attached to this waveguide sensor, and the cloud points of four different oils within the temperature range from 30° C. to −10° C. were determined. The results are given in Table 2.

TABLE 2

| Type of oil | Emergence end No. | | | | | Refractive index at 20° C. |
|---|---|---|---|---|---|---|
| | 1 | 2 | 3 | 4 | 5 | |
| 1 Naphtha | o | o | o | o | — | 1.399 |
| 2 Kerosine | o | — | — | — | — | 1.436 |
| 3 Gas oil | — | — | — | — | — | 1.470 |
| 4 Paraffin | o | o | — | — | — | 1.425 | o = total reflection (ON)
— = transmission (OFF)

INDUSTRIAL APPLICABILITY

A small high-precision cloud point meter is provided which is characterized by a waveguide sensor of a total-reflection type and a cooling/heating means located in contact with the total-reflection type sensor to cool/heat it within a necessary temperature range. The detection is accurate because only the rays of light within a preset emergence angle range are detected in binary (on-off) fashion. Its heat capacity is small and the response is good. Temperature precision also is high. Continual high-speed cloud point response is made possible by rapid temperature control while the detection surface is kept in contact with the chemical product whose cloud point is to be determined. Compared with the conventional method of cloud point determination that takes about 60 minutes per measurement, the sensor of this invention remarkably shortens the period to but about 60 seconds. Similarly, cloud point determination can be accomplished with various petroleum and chemical products as well by setting the angles of incidence and reflection and also the refractive index of the waveguide so that when the deposition or separation of solid matter takes place, a corresponding change in the refractive index causes total reflection. The cloud point meter of this invention has a promising future, especially as such for petroleum products, well capable of replacing the conventional meters conforming to JIS.

What is claimed is:

1. In a cloud point meter comprising a waveguide sensor of a total-reflection type, a waveguide having an incidence channel, an emergence channel and a detection surface all formed on a substrate, the incidence channel and emergence channel intersecting along the detection surface, the detection surface coming in contact with a liquid whose cloud point is to be determined, an incidence optical fiber connected to the entrance of the incidence channel to introduce light into the channel, and an emergence optical fiber connected to the exit of the emergence channel to receive total-reflection light from the emergence channel; and a cooling/heating means in contact with the waveguide sensor to cool/heat the waveguide sensor within a desired temperature range.

2. The cloud point meter of claim 1 wherein the cooling/heating means is a Peltier element mounted on a heat sink, a heat exchanger which uses a circulating coolant, or a cryostat.

3. In a cloud point meter comprising a waveguide sensor of a total-reflection type which includes a substrate, an incidence region, an emergence region and a detection surface all formed on the substrate, the incidence region and emergence region both being formed adjacent to the detection surface, the detection surface coming into contact with a liquid whose cloud point is to be determined, a waveguide layer formed on the substrate to provide a waveguide having an incidence channel intersecting the incidence region and a plurality of emergence channels intersecting the emergence region, an incidence optical fiber connected to the entrance of the incidence channel to introduce light into the channel, and a plurality of emergence optical fibers connected to the respective exits of the emergence channels to receive total-reflection lights from the channels; and a cooling/heating means in contact with the waveguide sensor to cool/heat the waveguide sensor within a desired temperature range.

4. The cloud point meter of claim 3 wherein the cooling/heating means is a Peltier element mounted on a heat sink, a heat exchanger which uses a circulating coolant, or a cryostat.

5. The cloud point meter of claim 3 wherein the incidence region has the shape of a quadrant with a radius $r_1$, the emergence region has the shape of a quadrant with a radius $r_2$, and the plurality of emergence channels comprises an array of n emergence channels formed within an angular range from $(\theta_1-\alpha)$ to $(\theta_1+\beta)$, wherein $r_2(\alpha+\beta)/(n-1)\geq 18$, $\theta_2$ being a reflected angle in the emergence region which corresponds to an identical incidence angle in the incidence region, and $\alpha$ and $\beta$ being angles within the emergence region which define said angular range when the incidence angle is $\theta_1$.

6. A method of determining cloud points using a high precision cloud point meter comprising a waveguide sensor of a total-reflection type, the waveguide sensor including a waveguide having an incidence channel, an emergence channel and a detection surface all formed on a substrate, the incidence channel and emergence channel intersecting along the detection surface, an incidence optical fiber connected to the entrance of the incidence channel, and an emergence optical fiber connected to the exit of the emergence channel;

and a cooling/heating means in contact with the waveguide sensor for cooling/heating the waveguide sensor within a desired temperature range, the method comprising the steps of:

(a) placing a sample on the detection surface;

(b) introducing light into the incidence optical fiber, thereby introducing light into the incidence channel;

(c) detecting light in the emergence optical fiber, the light being received from the emergence channel;

(d) cooling/heating the waveguide sensor using the cooling/heating means, thereby cooling/heating the sample; and (e) determining the temperature wherein a total reflection of light occurs as detected in the emergence optical fiber, the temperature being the cloud point of the sample.

* * * * *